United States Patent [19]
Cruz

[11] Patent Number: 5,452,730
[45] Date of Patent: Sep. 26, 1995

[54] SURGICAL DRAINAGE BAG

[76] Inventor: Angel L. Cruz, HC-01 Box 7445, Las Piedras, Puerto Rico, 00771

[21] Appl. No.: 329,282

[22] Filed: Oct. 26, 1994

[51] Int. Cl.⁶ .................................................. A61B 19/00
[52] U.S. Cl. .................................. 128/849; 128/DIG. 24
[58] Field of Search .................................. 128/849–856, 128/DIG. 24

[56] References Cited

U.S. PATENT DOCUMENTS

| | | | |
|---|---|---|---|
| 2,936,757 | 5/1960 | Track | 128/DIG. 24 |
| 3,055,368 | 9/1962 | Baxter | 128/DIG. 24 |
| 3,660,033 | 5/1972 | Schwartz | 128/DIG. 24 |
| 3,837,342 | 9/1974 | Mitsuo | 128/DIG. 24 |
| 3,841,332 | 10/1974 | Treacle | 128/DIG. 24 |
| 4,372,313 | 2/1983 | Villari | 128/DIG. 24 |
| 5,107,859 | 4/1992 | Alcorn | 128/849 |
| 5,299,582 | 4/1994 | Potts | 128/849 |

FOREIGN PATENT DOCUMENTS 3743003  4/1989  Germany ........................ 128/DIG. 24

*Primary Examiner*—Michael A. Brown

[57] ABSTRACT

A surgical drainage bag formed of an elongate flexible transparent body having a first end spaced from a second end, and a front wall spaced from a rear wall, with the front wall including an opening directed therethrough adjacent the first end, and the opening having a surrounding adhesive layer, with a removable flexible layer positioned upon the adhesive layer permitting exposure of the adhesive layer for adherence onto a patient. A unitary sponge member having a slot directed therethrough is directed through a side wall of the bag structure permitting a drainage tube to be secured within the slot upon separation of the sponge member when directing the drainage tube therethrough. A drain tube positioned at a second end of the bag permits ease of drainage of fluid within the bag.

2 Claims, 4 Drawing Sheets

PRIOR ART

SURGICAL DRAINAGE BAG

TECHNICAL FIELD

The Field of invention relates to fluid collection bag structure, and more particularly pertains to a new and improved surgical drainage bag wherein the same is directed to the collection of bodily fluid relative to a wound opening.

BACKGROUND OF THE INVENTION

Prior art devices have been employed for fluid drainage such as indicated in U.S. Pat. No. 5,107,859 wherein a fluid collection bag has a foam opening support structure. U.S. Pat. No. 4,479,818 sets forth a further example of a fluid or surgical drainage bag structure with an opening and a vent in the rear wall of the bag structure.

U.S. Pat. No. 4,692,153 sets forth a surgical drain tube structure, with the U.S. Pat. No. 3,667,469 setting forth a further example of a surgical drainage pouch.

SUMMARY OF THE INVENTION

The surgical drainage bag of the invention comprises an elongate flexible transparent bag structure tapered from a first end to a second end, with the second end having a drain tube and plug. A first opening directed through a front wall of the bag adjacent the first end includes a circular adhesive surface in surrounding relationship relative to that opening, with a second opening configured as a slot directed through a unitary sponge member optionally employed, such that a drain tube may be directed through the slot when separating first and second sponge plates of the sponge member to effect drainage into the bag structure.

Objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DESCRIPTION OF THE PREFERRED EMBODIMENT

As required, detailed embodiments of the present invention are disclosed herein; however, it is to be understood that the disclosed embodiments are merely exemplary of the invention, which may be embodied in various forms. therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
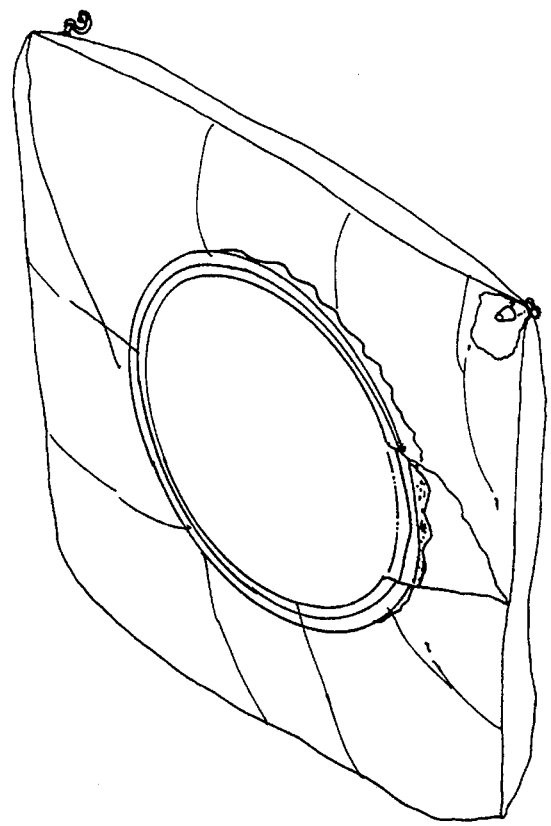
FIG. 1 is an isometric illustration of a prior art drain bag structure, such as indicated in the U.S. Pat. No. 5,107,859.
Figure 2:
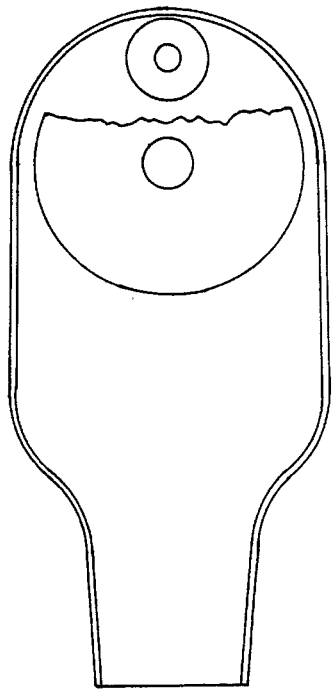
FIG. 2 is an orthographic view, taken in elevation, of a drain bag structure as indicated in U.S. Pat. No. 4,479,818.
Figure 3:
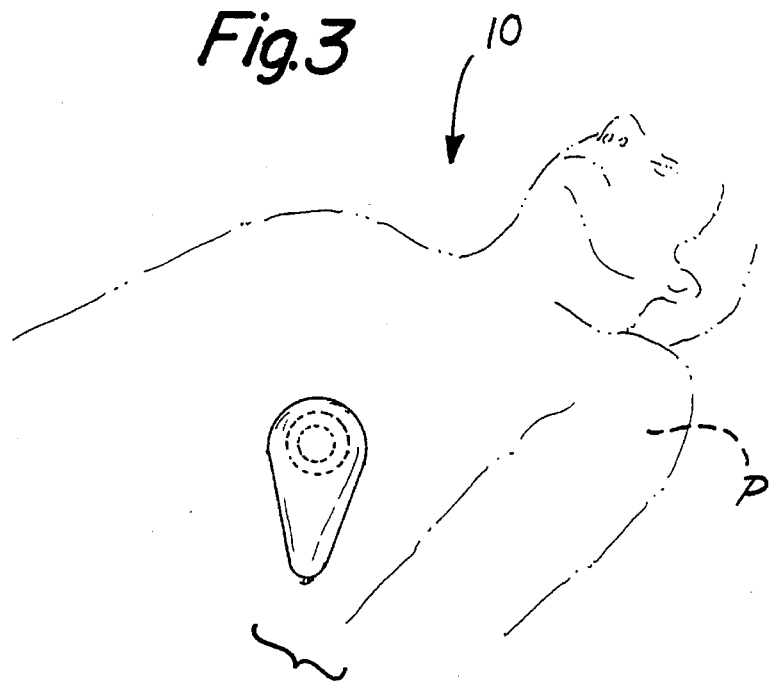
FIG. 3 is an isometric illustration of the invention in use.
Figure 4:
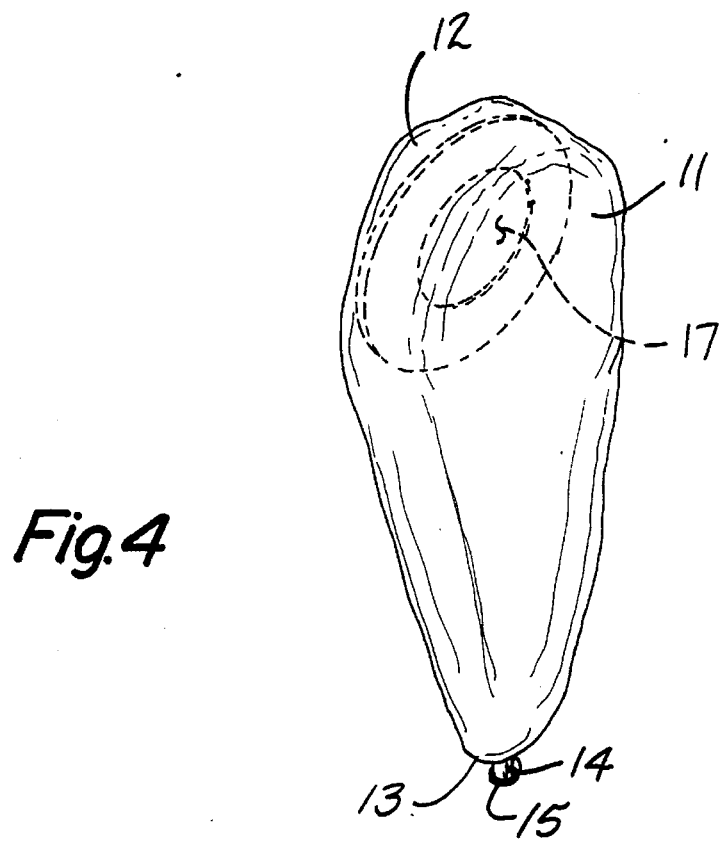
FIG. 4 is an enlarged isometric illustration of the invention.
Figure 5:
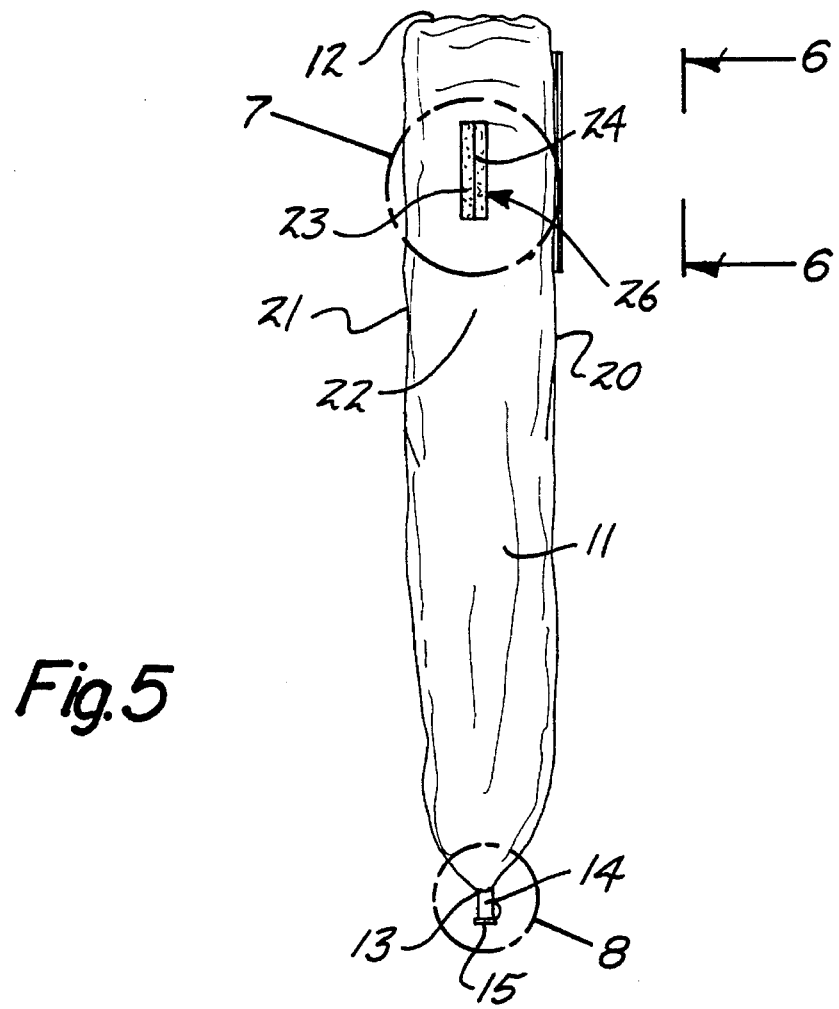
FIG. 5 is an orthographic side view, taken in elevation, of the invention.
Figure 8:
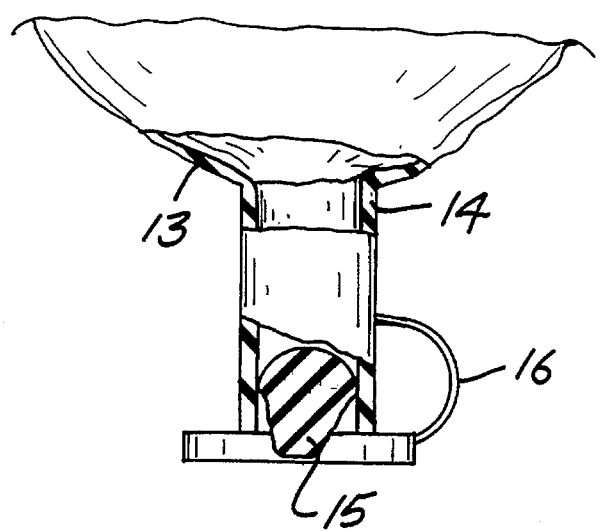
FIG. 8 is an enlarged orthographic view of section 8 as set forth in FIG. 5.

The surgical drainage bag 10 of the invention, such as indicated in the FIG. 3, is arranged for adherence to a patient "P". To this end, the bag structure is of a flexible elongate construction initiating as a base first end 12 and tapering to a second end 13, with the second end 13 having a drain tube 14 in communication to the interior cavity of the body 11, such that a plug cap 15 secured to the drain tube 14 by a tether line 16 is removably mounted to the drain tube 14 to permit drainage from within the body 11, such as indicated in FIG. 8.

Figure 6:
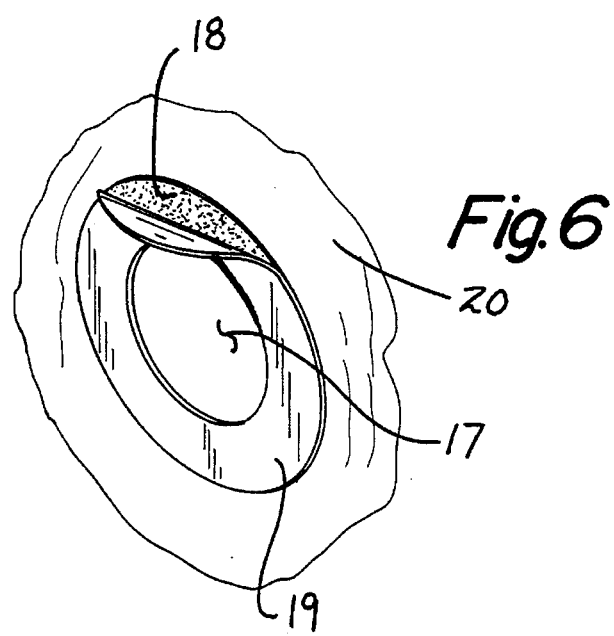
FIG. 6 is an isometric illustration, taken along the lines 6—6 of FIG. 5 in the direction indicated by the arrows.

A first opening 17 is directed through a front wall 20 of the bag structure adjacent to the first end 12. The front wall 20 is spaced from a rear wall 21, with spaced side walls 22 defining the bag structure. The first opening 17 (see FIG. 6) includes a surrounding adhesive surface 18 arranged in surrounding relationship relative to the first opening 17, with a peel-away flexible layer 19 arranged for removal relative to the adhesive surface 18 to expose that adhesive surface for adherence to the patient "P", with the opening 17 arranged to receive a wound and the like for permitting its drainage.

Figure 7:
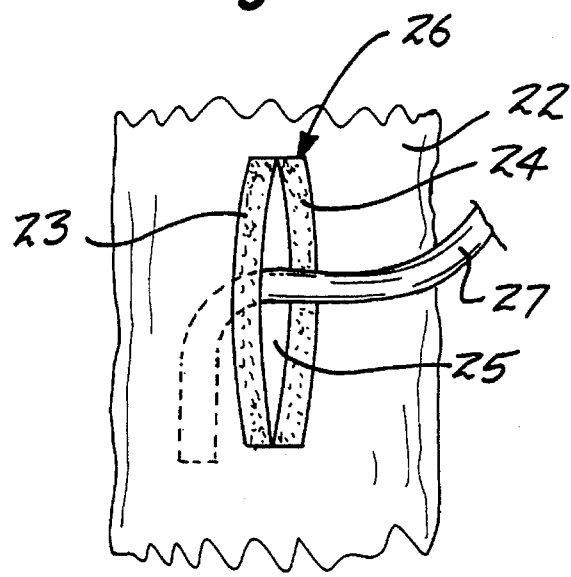
FIG. 7 is an enlarged orthographic view of section 7 as set forth in FIG. 5.

In the event of the use of a surgical drainage tube 27, as indicated in FIG. 7, a unitary sponge member 26 is directed through one of the side walls 22 adjacent to the first end 12. The use of a sponge member 26 has directed therethrough in a medial relationship a second opening 25 defining a slot (see FIG. 7), such that the unitary sponge member 26 is divided into first and second respective sponge plates 23 and 24 that are arranged in a coextensive mirror image relationship relative to one another that are biased towards one another to effect closure of the second opening 25 but may be displaced to receive the drainage tube 27. Such drainage tubes are well known use in the surgical arts and such is exemplified by the U.S. Pat. No. 4,692,153 for example incorporated herein by reference.

It should be noted that the surgical bag 10 having a tapering construction directs the thusly collected fluid at the second end 13 for ease of drainage relative to the bag structure through the drain tube 14, such that drainage of the bag may be effected periodically while the bag remains adhered to the patient "P", as illustrated in FIG. 3.

It is to be understood that while certain forms of the present invention have been illustrated and described herein, it is not to be limited to the specific forms or arrangement of parts described and shown.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed and desired to be protected by Letters Patent of the United States is as follows:

1. A surgical drainage bag, comprising, a flexible elongate body having a first end spaced from a second end, the first end tapering to the second end, and the bag having a bag cavity, with a drain tube secured to the second end, and a cap member, the cap member arranged for removal relative to the drain tube for permitting periodic drainage of fluid contained within the cavity, and the body having a front wall spaced from a rear wall and spaced side walls, and the front wall having an opening directed therethrough adjacent to the first end, with the opening including a surrounding adhesive surface fixedly secured to the front wall, and, and at least one of the side walls includes a sponge member, the sponge member oriented adjacent to the first end, having a slot directed through the sponge member, the slot dividing the sponge member into a first sponge plate and a second sponge plate arranged in a first position in contiguous mirror image confronting relationship relative to one another, with the first sponge plate and the second sponge plate arranged for separation relative to one another permitting a drain tube through the slot.

2. A drainage bag as set forth in claim 1 wherein the bag is transparent.

* * * * *